(12) United States Patent
Wong et al.

(10) Patent No.: US 6,744,053 B2
(45) Date of Patent: Jun. 1, 2004

(54) PET CAMERA WITH INDIVIDUALLY ROTATABLE DETECTOR MODULES AND/OR INDIVIDUALLY MOVABLE SHIELDING SECTIONS

(75) Inventors: Wai-Hoi Wong, Houston, TX (US); Jorge Uribe, Houston, TX (US); Hossain Baghaei, Sugarland, TX (US); Hongdi Li, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/040,905

(22) Filed: Jan. 7, 2002

(65) Prior Publication Data

US 2002/0148970 A1 Oct. 17, 2002

Related U.S. Application Data

(60) Provisional application No. 60/262,009, filed on Jan. 16, 2001.

(51) Int. Cl.[7] ................................................. G01T 1/00
(52) U.S. Cl. ............. 250/394; 250/363.03; 250/363.04
(58) Field of Search ..................... 250/363.03, 363.04, 250/363.05, 363.1, 505.1, 394

(56) References Cited

U.S. PATENT DOCUMENTS

| | | | | |
|---|---|---|---|---|
| 4,204,123 A | * | 5/1980 | Stoddart ................ | 250/363.04 |
| 4,227,088 A | | 10/1980 | Maydan et al. | |
| 5,444,252 A | * | 8/1995 | Hug et al. ............... | 250/363.08 |
| 5,825,031 A | | 10/1998 | Wong et al. ............ | 250/363.03 |
| 5,998,792 A | | 12/1999 | DiFilippo ............... | 250/363.05 |
| 6,114,701 A | | 9/2000 | Plummer et al. | |
| RE37,474 E | * | 12/2001 | Hug et al. .............. | 250/363.08 |
| 2003/0001098 A1 | * | 1/2003 | Stoddart et al. ....... | 250/363.04 |

OTHER PUBLICATIONS

Uribe et al., "Basic imaging performance characteristics of a variable field of view PET camera using quadrant sharing detector design," *IEEE Transactions on Nuclear Science*, 46:491–497, 1999.

Uribe et al., "Effect of the rotational orientation of circular photomultipliers in a PET camera block detector design," *IEEE Transactions on Nuclear Science*, 44:1266–1270, 1997.

Wong et al., "Design of a variable field prototype PET camera," *IEEE Transactions on Nuclear Science*, 43:1915–1920, 1996.

* cited by examiner

*Primary Examiner*—Diego Gutierrez
*Assistant Examiner*—Tania Courson
(74) *Attorney, Agent, or Firm*—Fulbright & Jaworski, LLP

(57) ABSTRACT

Systems and methods are described for a positron emission tomography camera with individually rotatable detector modules and/or individually movable shielding sections. An apparatus, includes a detector ring including a plurality of individually movable detector modules. Another apparatus, includes a radiation shield including a plurality of individually moveable shield sections. A method, includes generating an emission image of a sample; generating a transmission image of said sample while generating said emission image of said sample; and then correcting said emission image with said transmission image.

36 Claims, 6 Drawing Sheets

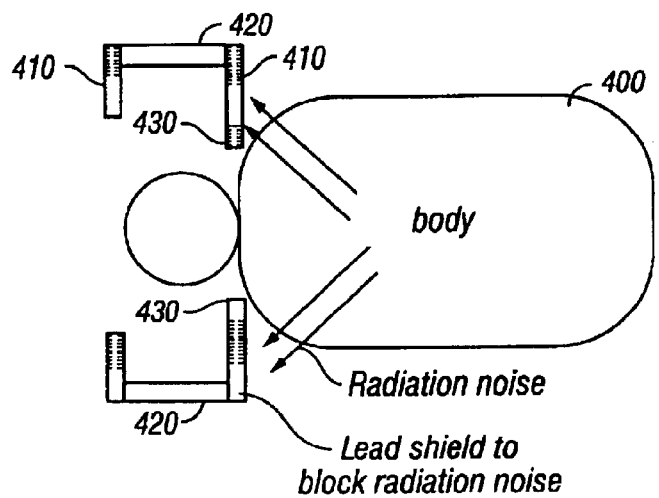
FIG. 4B
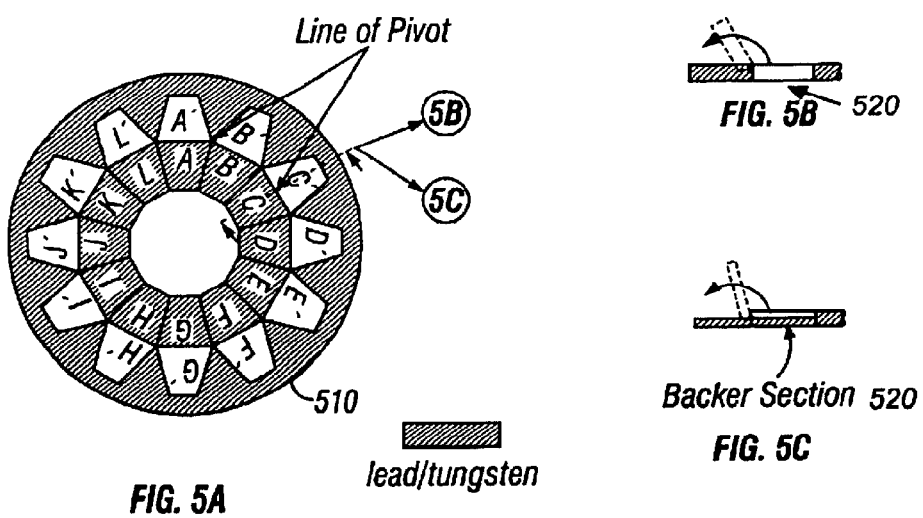
FIG. 5A  FIG. 5B  FIG. 5C

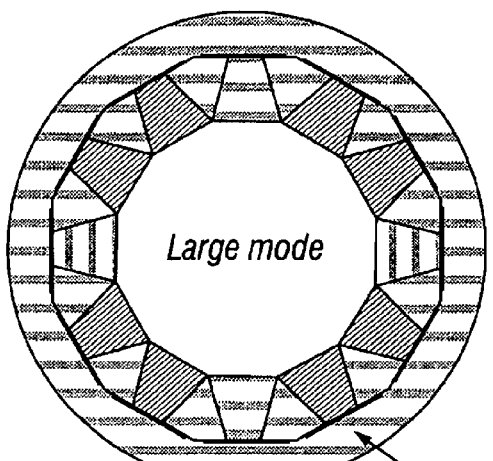
FIG. 6A  Side view detector module
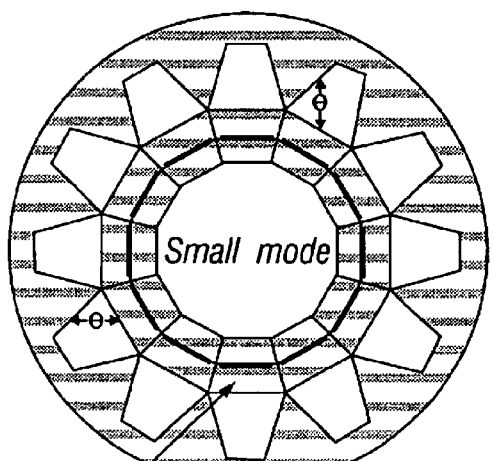
Side view detector module  FIG. 6B
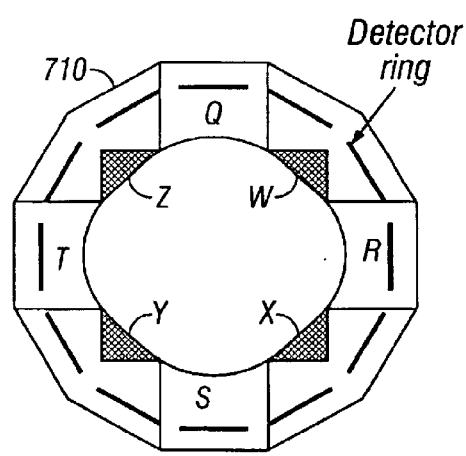
Large mode
FIG. 7A
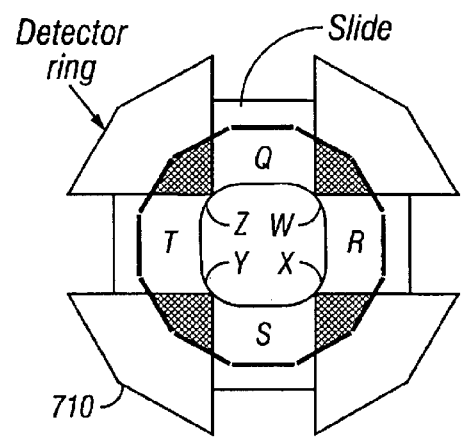
Small mode
FIG. 7B

PET CAMERA WITH INDIVIDUALLY ROTATABLE DETECTOR MODULES AND/OR INDIVIDUALLY MOVABLE SHIELDING SECTIONS

CROSS-REFERENCE TO RELATED APPLICATION

This application is related to, and claims a benefit of priority under 35 U.S.C. 119(e) and/or 35 U.S.C. 120 from, provisional patent application, U.S. Serial No. 60/262,009, filed Jan. 16, 2001, the entire contents of which are hereby expressly incorporated by reference for all purposes.

BACKGROUND OF THE INVENTION

1. Field of the Invention

The invention relates generally to the field of medical and/or biomedical research imaging. More particularly, a preferred embodiment of the invention is directed to a positron emission tomography (PET) camera with individually rotatable detector modules and/or movable shielding sections. The invention thus relates to a PET camera of the type that can be termed convertible.

2. Discussion of the Related Art

Positron emission tomography, sometimes called PET, is known to those skilled in the art. For instance, a conventional PET camera typically includes a detector ring having a number of detector modules.

A problem with this technology has been that typical PET samples to be imaged are of widely varying sizes. With regard to a human patient, a whole body scan must consider a much larger sample space than a head or breast scan. The larger sample space necessitates a detector ring, and detector noise shield of large radius. A major use of PET cameras is for whole body imaging for the purpose of tumor localization. Conversely, the smaller sample space defined by a head or breast can be accommodated within a smaller detector ring. Further, biomedical research imaging can generally be performed with a detector ring of relatively small radius. A small laboratory animal (e.g., a mouse) can be imaged with a detector ring of relatively small radius.

While many samples can be imaged with a small detector ring, a clinically useful instrument should provide a large detector ring radius to accommodate the largest sample, for example the whole body of an obese patient. On the other hand, when imaging a small sample, the level of signal detected by a detector ring with a large radius will be lower due to the increased distance between the sample and the detector ring, and the level of noise in the data can be higher due to the large radius of the noise shield. A large radius shield makes the detector more wide open to receive scattered radiation noise. Therefore, what is required is an approach that permits samples of widely varying sizes to be imaged by a detector ring with a variable radius.

One technique that has been used to vary the radius of a detector ring is to subdivide the detector ring into a number of detector modules that are radially repositionable.[1-3] A limitation of this technique has been that increasing the radius of a detector ring to accommodate larger samples causes gaps to be opened up between the individual detector modules that compose the ring. Optimal imaging is performed with a fully populated detector ring. That design would form a close packed ring for small objects but form a ring with gaps for large samples. That design is optimal for small samples but sub-optimal for large samples; the detector gaps reduce detector sensitivity and they cause image artifacts. Large gaps require macro-rotation of the detector ring as a whole, thereby increasing the time required for complete imaging. Therefore, what is also required is an approach that can vary the radius of a detector ring without creating gaps between the detectors or creating only a minimum amount of gap.

Another problem with this technology has been that the mass of the sample absorbs much of the emitted radiation. Thus, an emission image, of radioisotope in a patient for example, must be corrected with data from a transmission image, of a controlled radiation source which is typically located outside the sample. The transmission image is then used to correct the emission image. The need to obtain the transmission image increases the total amount of time required to process one sample. Therefore, what is also required is an approach that can simultaneously perform both emission and transmission imaging.

Heretofore, the requirements of a variable detector ring radius, avoidance and/or minimization of gaps within the detector ring, and simultaneous emission and transmission imaging referred to above have not been fully met. What is needed is a solution that addresses these requirements, depending on the imaging situation.

SUMMARY OF THE INVENTION

A goal of the invention is to satisfy the requirements of a variable detector ring radius, avoidance and/or minimization of gaps within the detector ring, protecting a variable detector ring with a corresponding variable detector shield, increasing the axial extent of the camera in some situations, and simultaneous emission and transmission imaging which, in the case of the prior art have not been fully satisfied.

One embodiment of the invention is based on an apparatus, comprising a detector ring including a plurality of individually movable detector modules. Another embodiment of the invention is based on a method, comprising: converting a detector ring including moving at least one of a plurality of independently movable detector modules. Another embodiment of the invention is based on a computer program comprising computer program means adapted to perform the steps of converting a detector ring including moving at least one of a plurality of independently movable detector modules when said program is run on a computer. Another embodiment of the invention is based on an apparatus, comprising a radiation shield including a plurality of individually moveable shield sections. Another embodiment of the invention is based on a method, comprising: reconfiguring a radiation shield including moving at least one of a plurality of independently movable shield sections. Another embodiment of the invention is based on a computer program comprising computer program means adapted to perform the steps of reconfiguring a radiation shield including moving at least one of a plurality of independently movable shield sections when said program is run on a computer. Another embodiment of the invention is based on a method, comprising: generating an emission image of a sample; generating a transmission image of said sample while generating said emission image of said sample; and then correcting said emission image with said transmission image.

These, and other, aspects of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

BRIEF DESCRIPTION OF THE DRAWINGS

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference numerals (if they occur in more than one view) designate the same elements. It should be noted that the features illustrated in the drawings are not necessarily drawn to scale.

FIGS. 4A and 4B illustrate schematic views of an assembly of detector modules and shields in two different modes, representing embodiments of the invention.

FIGS. 5A–5C illustrate schematic views of a shield annulus, representing an embodiment of the invention.

FIGS. 6A and 6B illustrate schematic views of a detector module and shield assembly in two different modes, representing embodiments of the invention.

FIGS. 7A and 7B illustrate schematic views of another detector and shield assembly in two different modes, representing embodiments of the invention.

DESCRIPTION OF PREFERRED EMBODIMENTS

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

Within this application several publications are referenced by superscripts composed of Arabic numerals within parentheses. Full citations for these, and other, publications may be found at the end of the specification immediately preceding the claims after the section heading References. The disclosures of all these publications in their entireties are hereby expressly incorporated by reference herein for the purpose of indicating the background of the invention and illustrating the state of the art.

The below-referenced U.S. patents discloses embodiments that were satisfactory for the purposes for which they are intended. The entire contents of U.S. Pat. Nos. 5,998,792 and 5,825,031 are hereby expressly incorporated by reference herein for all purposes.

The context of the invention can include medical imaging and/or biomedical research. The context of the invention can include positron emission tomography.

Individually Rotatable Detector Modules

The invention can be embodied in a positron emission tomography (PET) camera with a convertible field of view in both transaxial and axial dimensions. The term convertible, as used herein, can be defined as reconfigurable. Such a PET camera can be converted from a configuration (mode) which has a large transaxial field of view (e.g., whole body imaging) to another configuration (mode) that has a smaller transaxial field of view (e.g., brain/breast/small animal) but a large axial field of view. This convertibility can optimize PET imaging for both the whole-body (large transaxial field) and brain/breast/animal (small transaxial field) configurations (modes).

The invention can be embodied in a convertible positron emission tomography (PET) camera used for medical and biomedical research imaging. Such a PET camera can be a dedicated PET camera with a complete (fully populated) detector ring.

Another problem with current PET technology is that image quality is limited by the number of two events (coincidence) detected, which is also dependent on the axial width of the detector ring. Hence, whenever possible it is highly desirable to increase the axial extent of the detector ring to further improve image quality. Conventional PET detector rings have a fixed axial extent which is more limiting on image quality.

Figure 1A:
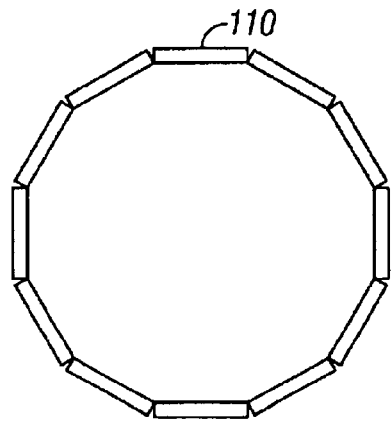
FIGS. 1A and 1B illustrate high level schematic views of a set of detectors in two different modes, representing embodiments of the invention.
Figure 1B:
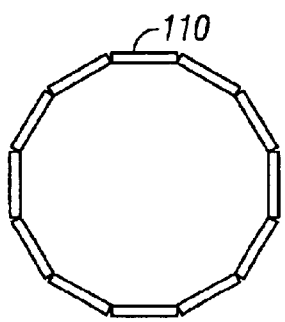

Referring to FIGS. 1A and 1B, a set of detector modules 110 are depicted in two different modes. A conversion between the modes can be effected by individually rotating the modules 90° and radially displacing the modules. The set of detector modules 110 can compose a detector ring.

Referring to FIG. 1A, a large mode is defined by arranging the detector modules 110 with their longer rectilinear dimension end to end. This arrangement defines a detector mode having a larger interior diameter. This mode can be termed whole body.

Referring to FIG. 1B, a small mode is defined by arranging the detector modules 110 with their shorter rectilinear dimension end to end. This arrangement defines a detector mode having a smaller interior diameter and a larger axial extent. This mode can be termed a brain, breast and/or small-animal mode.

Referring to FIGS. 1A and 1B, such a PET camera can be converted from a large whole body PET camera, (i.e. the detector ring is large enough to circumscribe the largest body cross-section) to a dedicated brain/breast PET with a smaller detector ring with enhanced image quality due to the larger axial extent and closer proximity to the smaller sample. In both modes (large and small), the detector rings can be fully populated with little or no detector ring gap(s). Hence, the invention can facilitate optimal imaging of both a whole-body type sample and a smaller brain/breast/small-animal type sample with enhanced quality.

Figure 2A:
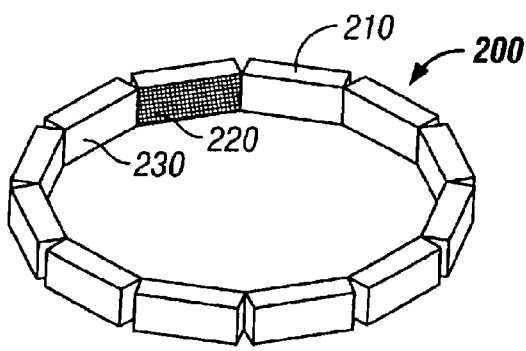
FIGS. 2A, 2B and 2C illustrate schematic perspective views of detector modules in different modes, representing embodiments of the invention.

Referring to FIG. 2A, a detector ring 200 can include a plurality of detector modules 210. Each of the detector modules can include a plurality of detectors 220. The detectors 220 of a given detector module 210 can compose a detector facet 230. The detector ring 200 can define a primary axis which passes through the center of the detector ring 200 and is substantially perpendicular to a plane defined by the detector ring 200.

Figure 2B:
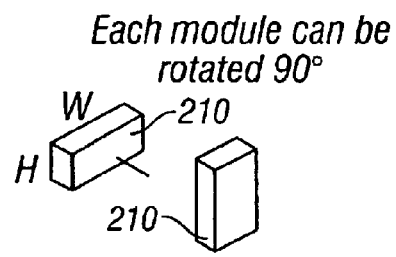

Referring to FIG. 2B, it is important to understand that each of the detector modules 210 can be rotated 90°. In this way, the detector ring can be converted between modes. The width W of each detector module 210 can define a longer rectilinear dimension of that detector module. Similarly, the height H of each detector module 210 can define a shorter rectilinear dimension of that module. Referring again to FIG. 2A, in the wholebody mode, the detector modules 210 are arranged with their longer rectilinear dimensions W end-to-end.

Figure 2C:
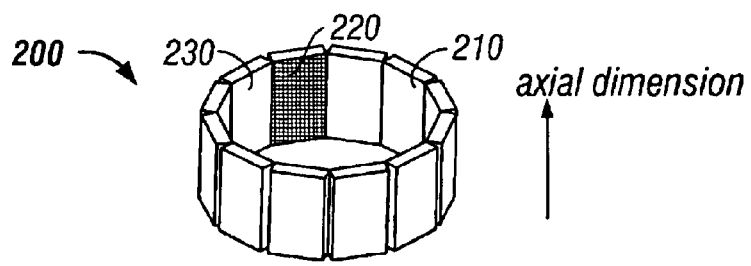

Referring to FIG. 2C, in the brain/breast/small-animal mode, the detector modules 210 are arranged with their shorter rectilinear dimensions H end-to-end. Since the detectors are closer to the smaller sample, the detector signal is higher which enhances the image quality. Since the long side W of the module is on the axial dimension, the axial extent of the small mode is increased to further enhance the images quality in this mode. The single headed arrow in FIG. 2C represents a positive displacement along an axial dimension that is at least substantially parallel to the primary axis.

Referring to FIGS. 2A–2C, to overcome geometric rotational constraints caused by the corners of adjacent detector modules preventing rotation, the detector modules need to be radially withdrawn away from a primary axis that is defined at the center of the detector ring. The modules need to be withdrawn to a standby position for at least a portion of time during which they are rotated between their small mode position and their large mode position. As soon as the detector modules clear each other during rotation they can begin to be radially converged to the radius of the chosen mode.

Twelve sections or detector modules are shown in FIGS. 2A–2C (the number of sections can be from approximately 3 to approximately 20). Of course, there can be more sections. Each module can be a two-dimensional matrix of small detectors 220 (the matrix can be composed of from hundreds to thousands of detectors). Each detector module 210 can be individually rotated 90° as shown in FIG. 2B, so that a transaxial row of detectors in the module for the whole-body mode will become an axial row of detectors in the brain/breast/animal mode. After the detector-module rotation, the modules can be displaced radially to reconstitute a detector ring of a different diameter. If, in the whole-body mode, the width of the module is 'W' in the transaxial dimension the height of the module is 'H'. The ratio of the small mode diameter '$D_S$' to the large mode diameter '$D_L$' can be approximately, $$\frac{D_S}{D_L} = \frac{H}{W}$$

Since the large and small diameters can be defined first, based on human size constraints, the ratio of H and W is thereby defined. The number of modules 'B' times 'W' should make a circle in which $$W \times B = \pi D_L$$

or $$B = (\pi D_L)/W$$

Similarly, $$B = (\pi D_S)/H$$

To be more accurate, since the detector ring is a polygon and not a perfect circle, $$B = 180°/\tan^{-1}(H/D_S) \quad (1)$$

$$B = 180°/\tan^{-1}(W/D_L) \quad (2)$$

The axial-field-of-view (AFOV) for the whole-body mode (i.e., 'H') is also a determining factor because it determines the total examination time which the camera takes to step through the whole-body for whole-body tumor localization, a major use of PET. Since 'B' has to be an integer number, $$180°/\tan^{-1}(H/D_S) = \text{integer} \quad (3)$$

If the axial-field-of-view for the large diameter (whole-body mode) is 9–12 cm (H), and the small diameter ($D_S$) is 40–50 cm, the optimal number of detector modules would be 12. If the axial-field-of-view for the large diameter (whole-body mode) is 14–17 cm (H) and with the same $D_S$, the optimal number of detector modules will be 8.

Since for the large mode, $$180°/\tan^{-1}(W/D_L) = \text{integer} \quad (4)$$

the integer in equations (3) and (4) should be equal in this design.

The detector diameters ($D_S$, $D_L$) of the two imaging modes can be related to the cross-sectional dimensions (H, W) of the detector module by the following relationship, $$\frac{D_S}{D_L} = \frac{H}{W}$$

The two axial-field-of-views of the camera should be equal to H and W.

The movable detector modules can, for example, be mounted on the end of racks that are radially traversed with pinions and individually rotated with stepping motors. Alternatively, the movable detector modules can be individually repositioned manually. Of course, the entire detector ring upon which the modules are mounted can be rotated about its primary axis and/or repositioned linearly.

When the number of detector modules is excessively low, the detector ring loses its quasi-circular shape, thereby compromising resolution. On the other hand, when the number of detector modules is excessively high, the detector ring becomes overly complicated and expensive due to the increased number of parts. Although the number of detectors modules can be as low as three to form a ring, the preferred number of detector modules is preferably from approximately 4 to approximately 20, more preferably from approximately 8 to approximately 16, most preferably approximately 12.

Individually Movable Shielding Sections

The invention can also be embodied in a radiation shield, preferably a side-shield design for a convertible PET camera. The detector ring (formed by the detector-modules) should be shielded to block radiation coming from regions outside the region to be imaged. Stray radiation will degrade the image quality.

Figure 3:
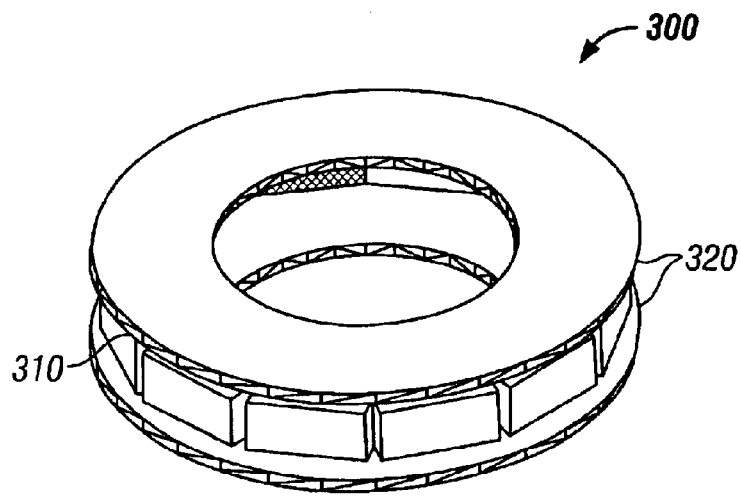
FIG. 3 illustrates a schematic perspective view of a PET camera detector ring with side shields, representing an embodiment of the invention.

Referring to FIG. 3, a detector ring 300 can be located between two side shields 320. The detector ring 300 can include a plurality of detector modules 310. Each of the side shields 320 can be composed of a plurality of shield sections.

If the detector ring geometry is convertible from a large diameter to a small diameter, it is preferably that the side-shields are also convertible. A convertible PET design would be of less practical significance if a different side-shield system weighing hundreds of pounds needed to be swapped out whenever the operating mode was changed. Ideally, the side-shields should follow the detector ring diameter (operating mode) to more effectively blocking the radiation noise from outside the region-of-interest.

Figure 4A:
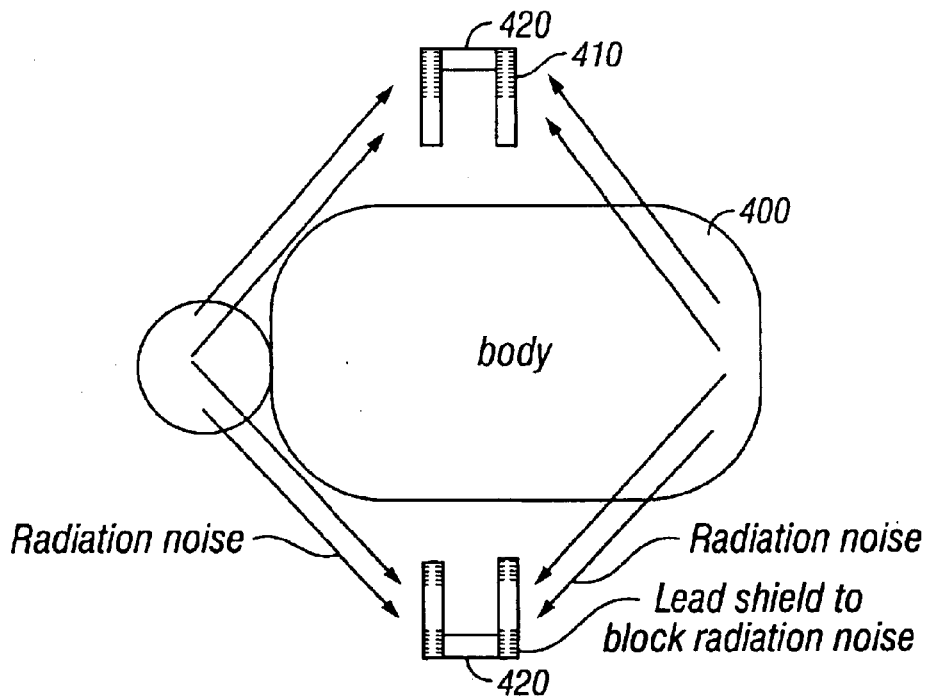

Referring to FIG. 4A, a human patient 400 is depicted within a detector ring 420. The detector ring 420 is shown in a large mode. Radiation noise from the head and the lower part of the body of the patient 400 is shown being intercepted by a pair of side shields 410 before it reaches the detector ring 420.

Referring to FIG. 4B, the detector ring 420 is shown in a small mode with the head of the human patient 400 under examination. Independently movable shield sections 430 are coupled to one of the side shields 410. The independently movable shield sections 430 serve to intercept additional radiation noise from parts of the patients of body which are not undergoing examination. Upon reconversion to the large mode, the independently movable shield sections 430 can be reconfigured (e.g., withdrawn inside the side shields 410).

A convertible side-shield system (CSSS) facilitates shielding change (e.g., polymorphic shielding). The convertible side-shield system can be used on, a convertible PET camera such as the one described here, other convertible PET designs such as described in U.S. Pat. No. 5,825,031, and conventional PET (fixed detector ring) designs. In all of these cases, the convertible side-shield system can optimally lower radiation noise when imaging different size objects. This is true even though the detector ring may not be adjustable.

Referring to FIG. 5A, an exemplary embodiment of the invention is depicted where a side shield 510 includes twelve independently movable shield sections A–L. Referring to FIG. 5B, it can be appreciated that each of the independently movable shield sections A–L is hinged with and extends from a mirror retracted position A'–L', in which each of the complementary sections A'–L' includes a backer section 520. As illustrated in FIG. 5C, the backer section 520 is included so that the shielding function of the mirror compliment remains even when the movable shield section is extended in toward the primary axis of the detector ring.

The shield sections can, for example, be mounted on bearing equipped hinges and pivoted with hydraulic pistons. Alternatively, the shield sections can be repositioned manually. Further, the hinged upon which the sections are mounted can in-turn be pivoted and/or repositioned linearly. Thus, one of a plurality of subassemblies of shield sections may be combined in the shape of a Z where the top two segments pivot while the lower section is radially traversed toward, or away, from the primary axis of a detector ring.

The particular material used for the shield sections should have a high cross section with regard to gamma radiation interaction. It is preferred that the shield section radiation absorbing material be lead or tungsten.

However, the particular material selected for shielding is not essential to the invention, as long as it provides the radiation shielding function. Normally, those who make or use the invention will select the best commercially available material based upon the economics of cost and availability, the expected application requirements of the final product, and the demands of the overall manufacturing process.

The invention can also utilize data processing methods that transform signals from a control unit to convert the detectors and/or reconfigure the shielding. For example, the invention can be combined with instrumentation to obtain state variable information to actuate interconnected discrete hardware elements. For instance, the positioning of the shielding can be interlocked to prevent operation of a PET camera unless the shielding is in a configuration that is appropriate for the mode in which the detector modules are positioned.

The invention can also be included in a kit. The kit can include some, or all, of the components that compose the invention. The kit can be an in-the-field retrofit kit to improve existing systems that are capable of incorporating the invention. The kit can include software/firmware and/or hardware for carrying out the invention. The kit can also contain instructions for practicing the invention. The components, software, firmware, hardware and/or instructions of the kit can be the same as those used in the invention.

The term approximately, as used herein, is defined as at least close to a given value (e.g., preferably within 10% of, more preferably within 1% of, and most preferably within 0.1% of). The term substantially, as used herein, is defined as at least approaching a given state (e.g., preferably within 10% of, more preferably within 1% of, and most preferably within 0.1% of). The term coupled, as used herein, is defined as connected, although not necessarily directly, and not necessarily mechanically. The terms including or having, as used herein, are defined as comprising. The term deploying, as used herein, is defined as designing, building, shipping, installing and/or operating. The term means, as used herein, is defined as hardware, firmware and/or software for achieving a result. The term program or phrase computer program, as used herein, is defined as a sequence of instructions designed for execution on a computer system. A program may include a subroutine, a function, a procedure, an object method, an object implementation, an executable application, an applet, a servlet, a source code, an object code, a shared library/dynamic load library and/or other sequence of instructions designed for execution on a computer system.

EXAMPLES

Specific embodiments of the invention will now be further described by the following, nonlimiting examples which will serve to illustrate in some detail various features of significance. The examples are intended merely to facilitate an understanding of ways in which the invention may be practiced and to further enable those of skill in the art to practice the invention. Accordingly, the examples should not be construed as limiting the scope of the invention.

Example 1

Referring to FIG. 6A, an exemplary embodiment of the invention is shown where twelve detectors are arranged in a large mode with gaps there between. In this large mode configuration, the individually movable shield sections are retracted so that the sample space diameter is maximized.

Referring to FIG. 6B, the detector modules have been individually rotated 90° and radially traversed toward the primary axis of the detector ring to assume the small mode configuration. In this configuration, the twelve individually movable shield sections have been hinged in toward the center of the detector ring. It can be appreciated that the sides of the individually movable shield sections mate with one another to provide continuous shielding across the detector modules from a point outside of the detector ring to a point inside the detector ring.

Referring to FIGS. 5A–5C and 6A–6B, instead of a solid annulus of lead or other shield material, the annulus has regular trapezoidal sections A, B, . . . L which can pivot. When the convertible camera is in the large wholebody mode where the detector ring is at a larger diameter, the trapezoidal sections of the side-shield are in positions A', B', . . . L', so that a complete annulus-shield is formed to shield the detector in the large diameter. When the camera is in the smaller mode, the trapezoidal sections of the shield will be flipped out along the pivot-line to form a smaller solid annulus to shield the detector ring in the smaller diameter. The angle "θ" of each trapezoidal section is determined by the number of sections, N, on the circle, θ=(180°–360°/N)/2. The height of each trapezoidal section will be determined by the shielding-aperture openings of both the large mode and the small mode. This design has N moving shielding sections.

Example 2

Referring to FIG. 7A, an exemplary embodiment of invention is shown where a set of twelve detector modules are arranged in a large mode. The side shield 710 of this embodiment includes four static shield sections. The side shield also includes four sliding shield sections Q–T. The side shield also includes four hinged shield sections W–Z.

Referring to FIG. 7B, in the small mode, the detector modules have been rotated and radially traversed toward the primary axis of the detector. In addition, the sliding shield sections Q–T have been moved in toward the primary axis as well. In addition, the hinged shield sections, W–Z have been pivoted in to fill the gaps between the sliding shields sections Q–T. In this way continuous shielding is provided from a point outside these small mode detector ring to a point inside the small mode detector ring.

The second convertible shield design has less moving sections. The design is shown below. Four sliding sections Q, R, S, T can slide radially. In the large mode, Q, R, S, T are slid to the large radius to form a solid annulus-shield. In the small mode, Q, R, S, T are slid to the small radius to shield the detectors in the small mode. In the small mode, the four small sections W, X, Y, Z, which do not weigh too much, can be placed manually into the shielding gaps between Q, R, S, T to complete the solid annulus. In the large mode, the four small sections W, X, Y, Z can be removed manually or flipped backed over the four fixed sections. This second convertible shielding design has less moving parts than the first design.

Another advantage or application of this second design is that even in the large mode (wholebody mode), the sliding shields Q, R, S, T can be slid as close to the patient body as possible so that it can block stray radiation coming from other organs more effectively. In a conventional PET shielding design, where the radiation shields are fixed with a very large aperture that is large enough to accommodate the largest cross-section of the largest size patient, the large aperture shielding is not very effective for imaging smaller patients or imaging the small body cross-section. This adjustable sliding design allows the shield to move closer to the smaller patients or body cross-section to provide a more effective shielding for different size patient or body cross-section.

Example 3

Figure 8A:
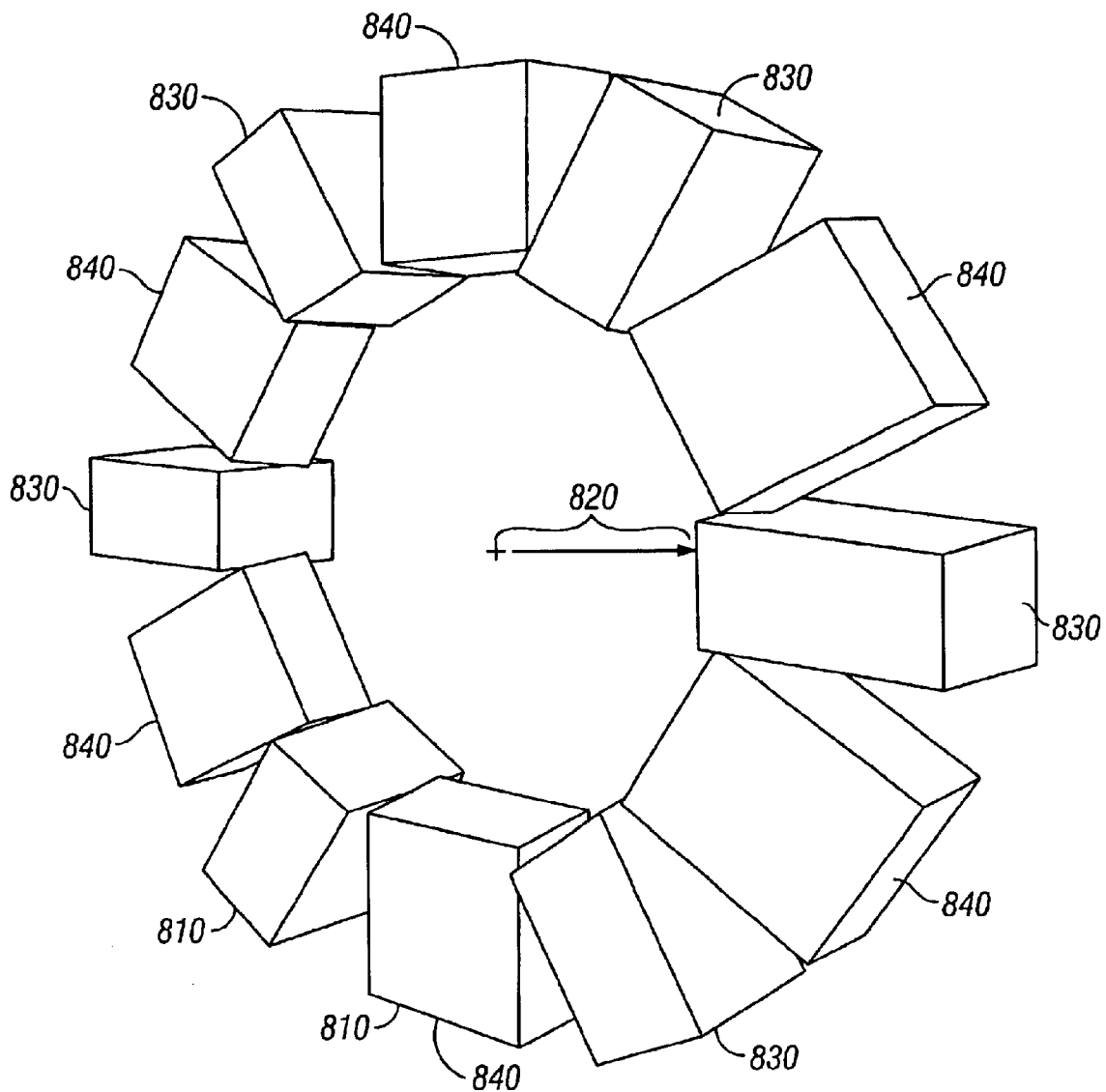
FIGS. 8A and 8B illustrate high level schematic views of a set of detectors in a mixed mode, representing an embodiment of the invention.
Figure 8B:
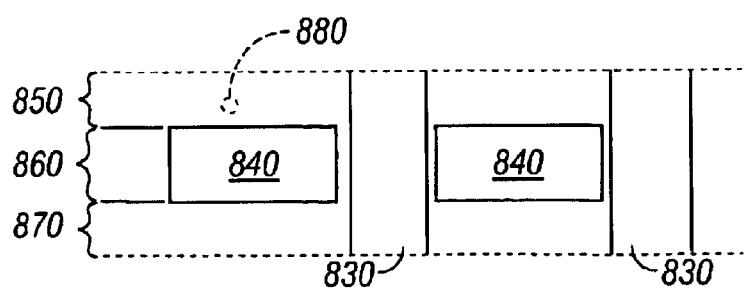

Referring to FIGS. 8A and 8B, an exemplary embodiment of invention is shown where a set of individually rotatable detector modules 810 can be positioned in a mixed mode. The same set of detectors can also be positioned in a large mode or a small mode. The mixed mode detector ring radius 820 is smaller than the corresponding large mode radius and larger than the corresponding small mode radius.

In the mixed mode, every other detector 830 has its detecting facet longer dimension substantially parallel to the primary axis. The remaining detectors 840 have their detecting facet longer dimensions substantially perpendicular to the primary axis.

Referring to FIG. 8B, a significant advantage of the mixed mode is that a transmission image can be generated while the emission image is being generated, thereby increasing patient/sample throughput. The emission image is generated by detector crystals located within the middle band 860. The transmission image is generated by detector crystals located within the edge bands 850 and 870. If transmission sources 880 (singles or coincidence sources) are located within the edge bands 850 and 870, the transmission data (either singles or coincidences) through the sample can be collected by the detectors in bands 850 and 870. The transmission source can have the shape of a point or a line or a ring with appropriate collimators and motion control. The transmission sources and the detector rings can be moved accordingly to provide the desirable transmission data sampling. A final PET camera image can be compiled with data from all of the bands 850, 860 and 870.

Example 4

Figure 9A:
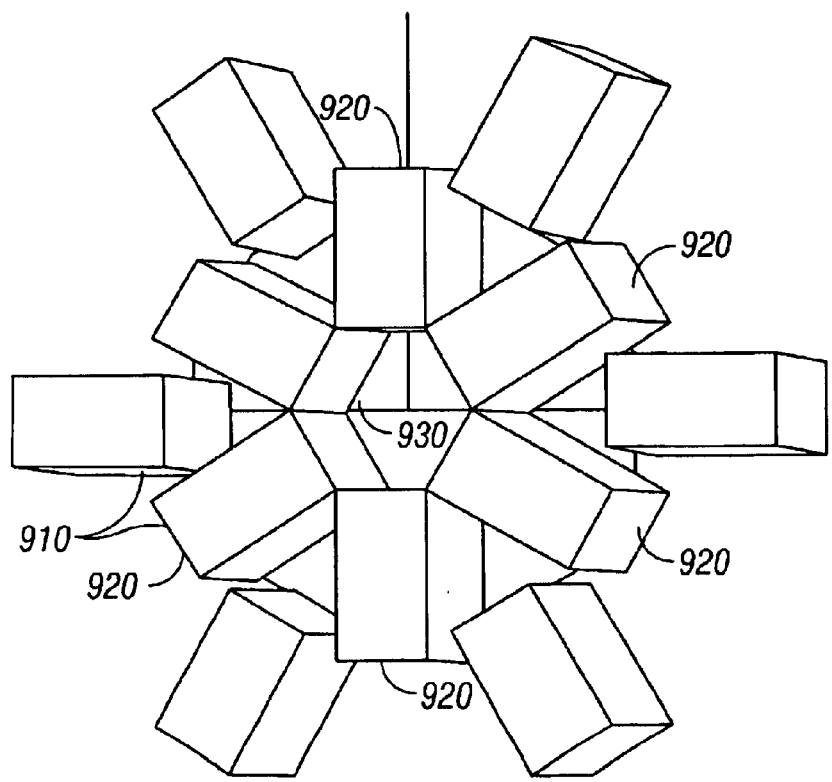
FIGS. 9A and 9B illustrate high level schematic views of a set of detectors in two different sub-small modes, representing embodiments of the invention.
Figure 9B:
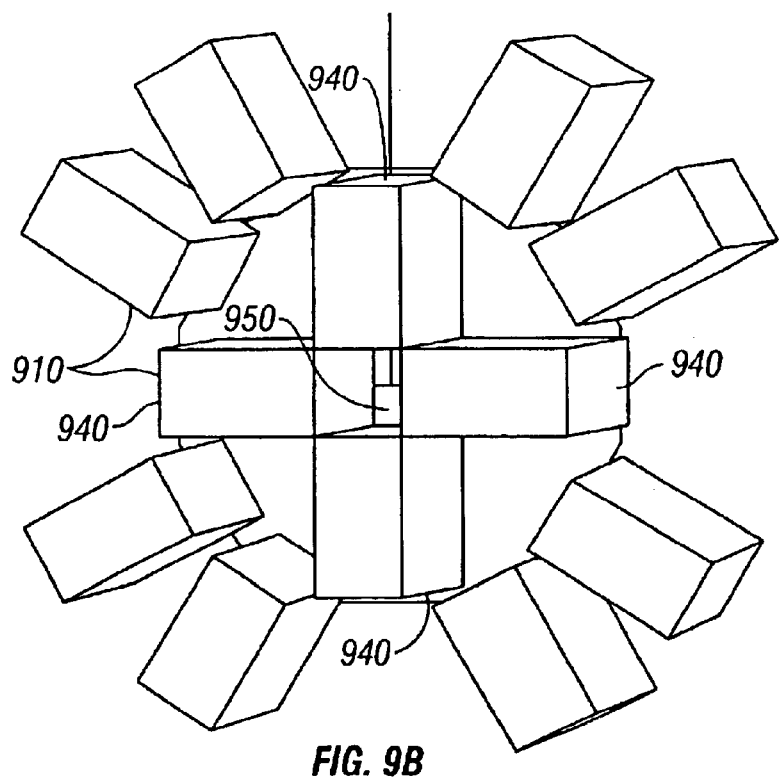

Referring to FIGS. 9A and 9B, an exemplary embodiment of invention is shown where another set of individually rotatable detector modules 910 can be positioned in alternative sub-small mode configurations. Such a detector ring composed of less than all the available modules can also be termed to define a super small mode.

In FIG. 9A, half of the 12 detectors 920 are positioned in a sub-small mode configuration to define a hexagonal detector ring space 930. The other half are withdrawn to a standby position.

In FIG. 9B, a third of the 12 detectors 940 are positioned in an alternative sub-small mode configuration to define a square detector ring space 950. Clearly, the hexagonal detector ring shown in FIG. 9A provides a larger sample space than the square detector ring of FIG. 9B.

Practical Applications of the Invention

A practical application of the invention that has value within the technological arts is medical imaging a patient for diagnostic purposes. Further, the invention is useful in conjunction with biomedical research imaging (such as are used for the purpose of detecting cancer in small laboratory animals), or in conjunction with experimental treatments (such as are used for the purpose of evaluating the effectiveness of drugs), or the like. There are virtually innumerable uses for the invention, all of which need not be detailed here.

Advantages of the Invention

An embodiment of the invention, can be cost effective and advantageous for at least the following reasons.

The design can have very high detection sensitivities for the small mode. For brain imaging the true-coincidence detection sensitivity will be increased by $(W/H)^2$ over the whole-body mode from the increase in axial-field-of-view, and another factor of $D_L/D_S$ because of the smaller ring geometry. Since $D_L/D_S$ is equal to W/H, the total increase in true-coincidence detection sensitivity is $(W/H)^3$ for 3-D PET imaging.

In the breast mode, the patient lies prone with the breast hanging down. For breast imaging, since the thorax is not in the field of view to attenuate the signal in this imaging mode, there is another factor of 4–6 higher sensitivity in additional to the factor $(W/H)^3$.

In this convertible design, there is no or very little gaps in the detector ring in both the large and small modes. In the former convertible design, there are large detector gaps in the large mode, which may cause detection sensitivity loss and some image artifacts when the gap is so big that even axially rotating the detection ring cannot compensate for. This convertible design eliminates these image artifacts and sensitivity loss.

Even with axial rotation, a moderately large detector gap still causes a nonuniformity of data sampling which needs to be corrected for in the image processing stage. This proposed solid-ring convertible design provides almost perfect data sampling as a conventional PET camera with a complete detection ring system, which improves image quality. However, a conventional PET cannot change the field of view to optimize the camera for different size subject. Hence, this design preserves the artifact-free-image characteristics of conventional PET while allowing the detector-ring geometry to change to optimize the detection efficiency for different size objects.

The adjustable shielding for blocking stray radiation (image-degrading noise) from other parts of the body can be optimized for each individual imaging procedure depending on patient sizes and body cross-section to be imaged. This will lower the noise in the image and increase the detection or diagnostic accuracy of the PET camera.

The individual movement capability of the detector modules permits a subset of the modules to be withdrawn out of the detector ring. The remaining modules can then define a detector ring of smaller radius. A detector ring of small radius allows good images of very small samples (e.g., a mouse).

All the disclosed embodiments of the invention described herein can be realized and practiced without undue experimentation. Although the best mode of carrying out the invention contemplated by the inventors is disclosed above, practice of the invention is not limited thereto. Accordingly, it will be appreciated by those skilled in the art that the invention may be practiced otherwise than as specifically described herein.

For example, the individual components need not be formed in the disclosed shapes, or combined in the disclosed configuration, but could be provided in virtually any shape, and combined in virtually any configuration. Further, the individual components need not be fabricated from the disclosed materials, but could be fabricated from virtually any suitable materials. Further, although the detector modules described herein can be separate modules, it will be manifest that the detector modules may be integrated into the system with which they are associated. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the invention may be made without deviating from the spirit and scope of the underlying inventive concept. It is intended that the scope of the invention as defined by the appended claims and their equivalents cover all such additions, modifications, and rearrangements.

The appended claims are not to be interpreted as including means-plus-function limitations, unless such a limitation is explicitly recited in a given claim using the phrase(s) "means for" and/or "step for." Expedient embodiments of the invention are differentiated by the appended subclaims.

REFERENCES

1. Basic Imaging Performance Characteristics of a Variable Field of View PET Camera Using Quandrant Sharing Detector Design, IEEE Transactions on Nuclear Science, Vol. 46, pages 491–497, (Jorge Uribe, Hossain Baghaei, Hongdi Li, Shigeru Yokoyama, Nan Zhang, Junming Wang, Frank R. Dobbs, Wai-Hoi Wong, 1999).
2. Design of a Variable Field Prototype PET Camera, IEEE Transactions on Nuclear Science, Vol. 43, pages 1915–1920, (W-H Wong, J. Uribe, W. Lu, G. Hu, K. Hicks, 1996).
3. Effect of the Rotational Orientation of Circular Photomultipliers in a PET Camera Block Detector Design, IEEE Transactions on Nuclear Science, Vol. 44, pages 1266–1270, (J. Uribe, W-H Wong, G. Hu, K. Hicks, J. Wang, H. Baghaei, N. Zhang, H. Li, S. Yokoyama, 1997).
4. Marks Mechanical Engineering Handbook, 10th ed., McGraw Hill, (Eugene A. Avallone et al. eds., 1996).
5. The Electrical Engineering Handbook, CRC Press, (Richard C. Dorf et al. eds., 1993).

What is claimed is:

1. An apparatus comprising a detector ring including a plurality of individually movable detector modules,
   wherein the detector ring has a small mode detector ring diameter $D_S$ and a large mode detector ring diameter $D_L$;
   wherein each of the plurality of individually movable detector comprises a longer dimension, W, and a shorter dimension, H; and
   wherein $HID_S$ is approximately equal to $W/D_L$.

2. The apparatus of claim 1, wherein said detector ring defines a primary axis and the plurality of individually movable detector modules include:
   a first rotatable detector module that is rotatable about a first module axis; and
   a second rotatable detector module that is rotatable about a second module axis.

3. The apparatus of claim 2, wherein said first module axis is substantially perpendicular to said primary axis and said second module axis is substantially perpendicular to said primary axis.

4. The apparatus of claim 2, wherein
   said first rotatable detector module is repositionable between a first detector large mode position, wherein a longer dimension of the first rotatable detector module is substantially perpendicular to said primary axis, and a first detector small mode position, wherein said longer dimension of said first rotatable detector module is substantially parallel to said primary axis; and
   said second rotatable detector module is repositionable between a second detector large mode position, wherein a longer dimension of said second rotatable detector module is substantially perpendicular to said primary axis, and a second detector small mode position, wherein the longer dimension of said second rotatable detector module is substantially parallel to said primary axis.

5. The apparatus of claim 4, wherein there is substantially no gap between said first rotatable detector module and said second rotatable detector module when said first rotatable detector module is in said first detector large mode position and said second rotatable detector module is in said second detector large mode position.

6. The apparatus of claim 4, wherein there is substantially no gap between said first rotatable detector module and said second rotatable detector module when said first rotatable detector module is in said first detector small mode position and said second rotatable detector module is in said small mode position.

7. The apparatus of claim 4, wherein
   i) said first rotatable detector module is continuously rotatable between said first detector large mode position and said first detector small mode position and
   ii) said second rotatable detector module is continuously rotatable between said second detector large mode position and said second detector small mode position.

8. The apparatus of claim 7, wherein there is a gap between said first rotatable detector module and said second rotatable detector module when
   i) said first rotatable detector module is positioned between said first detector small mode position and said first detector large mode position and
   ii) said second rotatable detector module is positioned between said second detector small mode position and said second detector large mode position.

9. The apparatus of claim 8, wherein said first rotatable detector module is radially withdrawn from said primary axis to a first rotatable detector standby position for at least a portion of time during which said first rotatable detector module is rotated between said first detector small mode position and said first detector large mode position.

10. The apparatus of claim 8, wherein said second rotatable detector module is radially withdrawn from said primary axis to a second rotatable detector standby position for at least said portion of time during which said second rotatable detector module is rotated between said second detector small mode position and said second detector large mode position.

11. The apparatus of claim 2, wherein both said first rotatable detector module and said second rotatable detector module are radially displaceable with regard to the primary axis of the detector ring.

12. The apparatus of claim 11, wherein radial displacement of both said first rotatable detector module and said second rotatable detector module can occur simultaneously with individual rotation of both said first rotatable detector and said second rotatable detector.

13. The apparatus of claim 1, further comprising a plurality of individually moveable detector ring shield sections coupled to said detector ring.

14. The apparatus of claim 1, wherein
   i) said detector ring defines a primary axis,
   ii) a first subset of said plurality of individually movable detector modules can be positioned in a small mode position where the longer dimension of each module of said first subset are substantially parallel to said primary axis and
   iii) a second subset of said plurality of individually movable detector modules can be positioned in a large mode position where the longer dimension of each module of said second subset are substantially perpendicular to said primary axis.

15. The apparatus of claim 1, wherein
   i) said detector ring defines a primary axis,
   ii) a first subset of said plurality of individually movable detector modules can be positioned in a sub-small mode position and
   iii) a second subset of said plurality of individually movable detector modules can be positioned in a standby position, said second subset located further from said primary axis than said first subset.

16. The apparatus of claim 1, wherein the apparatus is a positron emission tomography camera.

17. A method, comprising:
   converting a detector ring including moving at least one of a plurality of independently movable detector modules;
   wherein the detector ring has a small mode detector ring diameter $D_S$ and a large mode detector ring diameter $D_L$;
   wherein each of the plurality of individually movable detector comprises a longer dimension, W, and a shorter dimension, H; and
   wherein $H/D_S$ is approximately equal to $W/D_L$.

18. The method of claim 17, wherein said detector ring defines a primary axis and converting includes rotating a first rotatable detector module about a first module axis and rotating a second rotatable detector module about a second module axis.

19. The method of claim 18, wherein said first module axis is substantially perpendicular to said primary axis and said second module axis is substantially perpendicular to said primary axis.

20. The method of claim 18, wherein converting includes:
   rotating said first rotatable detector module between a first detector large mode position, wherein a longer dimension of said first rotatable detector module is substantially perpendicular to said primary axis, and a first detector small mode position, wherein said longer dimension of said rotatable detector module is substantially parallel to said primary axis; and
   rotating said second rotatable detector module between a second detector large mode position, wherein a longer dimension of said second rotatable detector module is substantially perpendicular to said primary axis, and a second detector small mode position, wherein said longer dimension of said second rotatable detector module is substantially parallel to said primary axis.

21. The method of claim 20, wherein there is substantially no gap between said first rotatable detector module and said second rotatable detector module, when said first rotatable detector module is in said first detector large mode position and said second rotatable detector module is in said second detector large mode position.

22. The method of claim 20, wherein there is substantially no gap between said first rotatable detector module and said second rotatable detector module, when said first rotatable detector module is in said first detector small mode position and said second rotatable detector module is in said small mode position.

23. The method of claim 20, wherein
   i) said first rotatable detector module is continuously rotatable between said first detector large mode position and said first detector small mode position and
   ii) said second rotatable detector module is continuously rotatable between said second detector large mode position and said second detector small mode position.

24. The method of claim 23, wherein there is a gap between said first rotatable detector module and said second rotatable detector module, when
   i) said first rotatable detector module is positioned between said first detector small mode position and said first detector large mode position and ii) said second rotatable detector module is positioned between said second detector small mode position and said second detector large mode position.

25. The method of claim 18, further comprising radially displacing said first rotatable detector module with regard to said primary axis and radially displacing said second rotatable detector module with regard to said primary axis.

26. The method of claim 25, wherein said first rotatable detector module is radially withdrawn from said primary axis to a first rotatable detector standby position for at least a portion of time during which said first rotatable detector module is rotated between said first detector small mode position and said first detector large mode position.

27. The method of claim 25, wherein said second rotatable detector module is radially withdrawn from said primary axis to a second rotatable detector standby position for at least said portion of time during which said second rotatable detector module is rotated between said second detector small mode position and said second detector large mode position.

28. The method of claim 25, wherein radial displacement of both said first rotatable detector module and said second rotatable detector module can occur simultaneously with individual rotation of both said first rotatable detector and said second rotatable detector.

29. The method of claim 18, wherein said detector ring defines a primary axis and further comprising positioning
i) a first subset of said plurality of individually movable detector modules in a small mode position where the longer dimension of each module of said first subset is substantially parallel to said primary axis
ii) and a second subset of said plurality of individually movable detector modules in a large mode position where the longer dimension of each module of said second subset is substantially perpendicular to said primary axis.

30. The method of claim 18, wherein said detector ring defines a primary axis and further comprising positioning
i) a first subset of said plurality of individually movable detector modules in a sub-small mode position and
ii) a second subset of said plurality of individually movable detector modules can be positioned in a standby position, said second subset located further from said primary axis than said first subset.

31. The method of claim 17, further comprising moving at least one of a plurality of individually moveable detector ring shield sections that are coupled to said detector ring.

32. The method of claim 17, the method being performed using racks, pinions, and stepping motors.

33. The method of claim 17, further comprising executing a computer program that provides instructions to perform the step of converting the detector ring.

34. The method of claim 17, further comprising imaging a sample.

35. The method of claim 34, wherein a data file comprises an image of the sample.

36. A computer readable medium comprising computer executable instructions for converting a detector ring by moving at least one of a plurality of independently movable detector modules;

wherein the detector ring has a small mode detector ring diameter $D_S$ and a large mode detector ring diameter $D_L$;

wherein each of the plurality of independently movable detector modules comprises a longer dimension, W, and a shorter dimension, H; and wherein $H/D_S$ is approximately equal to $W/D_L$.

\* \* \* \* \*